(12) United States Patent
Valteau et al.

(10) Patent No.: US 10,502,393 B2
(45) Date of Patent: Dec. 10, 2019

(54) LOW-BULK OPTICAL COLLIMATOR FOR GENERATING A SMALL SPOT OF ILLUMINATION

(71) Applicant: Maquet SAS, Ardon (FR)

(72) Inventors: Cecilia Valteau, Ardon (FR); Minh Hong Vu Thi, Ardon (FR); David Genevriere, Ardon (FR)

(73) Assignee: MAQUET SAS (FR)

( * ) Notice: Subject to any disclaimer, the term of this patent is extended or adjusted under 35 U.S.C. 154(b) by 0 days.

(21) Appl. No.: 15/765,878

(22) PCT Filed: Jul. 27, 2016

(86) PCT No.: PCT/FR2016/051951
§ 371 (c)(1),
(2) Date: Apr. 4, 2018

(87) PCT Pub. No.: WO2017/068253
PCT Pub. Date: Apr. 27, 2017

(65) Prior Publication Data
US 2018/0283653 A1    Oct. 4, 2018

(30) Foreign Application Priority Data

Oct. 20, 2015   (FR) ..................................... 15 60001

(51) Int. Cl.
*F21V 7/00*     (2006.01)
*F21V 5/04*     (2006.01)
(Continued)

(52) U.S. Cl.
CPC ............ *F21V 7/0091* (2013.01); *A61B 90/30* (2016.02); *F21V 5/04* (2013.01); *G02B 19/0028* (2013.01);
(Continued)

(58) Field of Classification Search
CPC ..... F21V 7/0091; F21V 5/04; G02B 19/0061; G02B 19/0028; G02B 27/30; A61B 90/30
See application file for complete search history.

(56) References Cited

U.S. PATENT DOCUMENTS 8,430,536 B1 *   4/2013   Zhao ................... G02B 19/0028
                                                              362/308
2008/0316761 A1 *  12/2008  Minano ................ G02B 3/0068
                                                              362/518

(Continued)

FOREIGN PATENT DOCUMENTS

CN    102 537 843 A    7/2012
WO    2016/057580 A1   4/2016

*Primary Examiner* — Anabel Ton
(74) *Attorney, Agent, or Firm* — Ware, Fressola, Maguire & Barber LLP

(57) ABSTRACT

A lighting device comprises a solid optical collimator (6'), the collimator comprises a truncated cap having an inside surface (10') operating in total internal reflection and having a small base opening into a frustoconical through recess that is coaxial with the cap and at the centre of which a light source (8') is placed, and having a refractive large base such that incident light emitted by the light source is guided in totality by the inside surface towards the large base of the cap. The recess of the collimator is disposed in the cap in such a manner as to have a small base open and coinciding with the small base of the cap.

17 Claims, 1 Drawing Sheet

(51) Int. Cl.
*G02B 19/00* (2006.01)
*A61B 90/30* (2016.01)
*G02B 27/30* (2006.01)
*F21W 131/205* (2006.01)
*F21Y 101/00* (2016.01)

(52) U.S. Cl.
CPC ......... *G02B 19/0061* (2013.01); *G02B 27/30* (2013.01); *F21W 2131/205* (2013.01); *F21Y 2101/00* (2013.01)

(56) References Cited

U.S. PATENT DOCUMENTS

| | | |
|---|---|---|
| 2009/0128921 A1 | 5/2009 | Roth |
| 2011/0026130 A1* | 2/2011 | Winston ............... G02B 17/006 359/641 |
| 2014/0036510 A1 | 2/2014 | Preston et al. |
| 2014/0204587 A1 | 7/2014 | Hukkanen |
| 2015/0204516 A1* | 7/2015 | Shen ....................... F21V 13/04 362/309 |
| 2016/0116139 A1* | 4/2016 | Zhao ....................... F21V 5/045 362/309 |
| 2016/0327236 A1* | 11/2016 | Benitez ..................... F21V 5/04 |
| 2017/0321865 A1* | 11/2017 | Parker .................... F21V 7/0016 |
| 2018/0017717 A1* | 1/2018 | Dross .................... G02B 3/0043 |

* cited by examiner

LOW-BULK OPTICAL COLLIMATOR FOR GENERATING A SMALL SPOT OF ILLUMINATION

CROSS REFERENCE TO RELATED APPLICATIONS

This application is the U.S. National Stage of International Application Number PCT/FR2016/051951 filed on Jul. 27, 2016, which application claims priority under 35 USC § 119 to French Patent Application No. 1560001 filed on Oct. 20, 2015. Both applications are hereby incorporated by reference in their entirety.

TECHNICAL FIELD

The invention relates to a solid optical collimator, comprising a truncated cap having an inside surface operating in total internal reflection and having a small base opening into a frustoconical through recess that is coaxial with the cap and at the centre of which a light source is to be placed, and having a refractive large base such that incident light emitted by the light source is guided in totality by the inside surface towards the large base of the cap.

The invention also relates to lighting devices including such optical collimators, and in particular surgical lighting devices used, in particular, for illuminating a medical operative field.

PRIOR ART

In known manner, in a lighting device for illuminating a medical operative field, one or more optical systems are provided in a lighting dome for causing the light emitted by a light source to converge on the operative field, in particular so as to form an illumination spot of larger or smaller size.

That optical system is generally a solid standard collimator that is in the form of a truncated cap having an inside surface operating in total internal reflection, the cap having a frustoconical recess that is coaxial with the cap, the large base of the truncated cone being open and coinciding with the small base of the cap. The light source is placed above the opening in the truncated cone, at the level of the tip of the cap. A lens that is coaxial with the cap is arranged below the truncated cone in such a manner as to refract light beams towards the operative field.

Presently, there is a demand from the medical world to have surgical lighting capable of providing illumination spots that are small, of the order of a few centimeters, for illuminating a zone of the body where small incisions are made, for example. It is known that with a standard collimator as described above and a given light-emitting diode (LED) as the light source, it is necessary to increase the height and the diameter of the standard collimator in order to form an illumination spot that is small relative to a standard collimator that gives an illumination spot that is large. The "small illumination spot" standard collimator is therefore much more voluminous than the "large illumination spot" standard collimator. Manufacturers of surgical lighting devices are seeking to reduce the volumes and the weights of lighting domes in order to make them easier for medical staff to manipulate above an operative field. The additional volume and weight brought by a "small illumination spot" standard collimator is not compatible with the demand for a lighting dome that is as slim and as lightweight as possible.

In addition, solid standard collimators as described above are made of injection-molded plastic. The cost of a part made of injection-molded plastic is closely linked to its thickness because its thickness has an impact on the injection-molding time. Thus, since a "small illumination spot" standard collimator has a height greater than the height of a "large illumination spot" standard collimator, and since that lengthens its production time, its manufacturing cost is increased.

Finally, in a standard collimator, it is known that, in the vicinity of the LED, rays reflected on the cone by Fresnel reflection loss go through the lens and take a non-useful optical path so that they create an interfering halo on the operative field that is unpleasant for the medical staff.

From various documents, lighting devices are known that have collimators that are modified in comparison to a solid standard collimator, but such collimators still do not make it possible to satisfy correctly the demand for small illumination spots.

SUMMARY OF THE INVENTION

An object of the invention is to remedy those drawbacks by proposing a solid optical collimator that has a novel structure.

To this end, the invention provides a surgical lighting device forming an illumination spot and comprising a lighting dome having a plurality of lighting devices, the surgical lighting device being characterized in that each lighting device includes a solid optical collimator comprising a truncated cap having an inside surface operating in total internal reflection and having a small base opening into a frustoconical through recess that is coaxial with the cap and at the centre of which a light source is placed, and having a refractive large base such that incident light emitted by the light source is guided in totality by the inside surface towards the large base of the cap, in that the recess of the collimator is disposed in the cap in such a manner as to have a small base open and coinciding with the small base of the cap, and in that the collimators are directed to concentrate the light flux from the light sources onto the illumination spot that is centered on the illumination axis of the lighting dome.

More particularly, in accordance with the invention:
the recess in the collimator opens out into the large base of said cap;
the recess comprises a frustoconical first recess having a small base open and coinciding with the small base of the cap, and a second coaxial recess under the first recess and, between the two recesses, an annular shoulder carries a screen for the incident light;
the screen is absorbent on its side closer to the light source;
the screen is diffusive on its side closer to the light source;
the screen is adhesively bonded to the shoulder;
the shoulder forms a plane surface that is perpendicular to the axis of the cap;
the collimator is rigid;
the collimator is made of injection-molded plastic;
the collimator is made of poly(methyl methacrylate) or "PMMA";
a support of the collimator includes means for fastening said screen for the incident light; and
the light source may be an LED.

With such an arrangement, the collimator is completely hollow axially, the recess being a through recess and being in part in the form of a truncated cone that is upside down relative to the truncated cone of a standard solid collimator. With this arrangement, the collimator has a hole instead of the lens that is normally arranged in a standard collimator.

With this arrangement, in a lighting device, the light source may be arranged very close to the collimator.

The collimator has a first useful optical interface that corresponds to the walls of the upside-down truncated cone that refract the light, the non-refracted light coming out through a hole on the large base side of the truncated cone; a second useful optical interface corresponding to the inside face of the outside surface of the collimator operating in total internal reflection; and an annular useful optical interface at the collimator outlet corresponding to the large base of the truncated cap and for refracting the light towards an operative field so as to form an illumination spot.

With this arrangement, the through recess is a superposition of two truncated cones aligned on a common axis with an open interface, or central hole, that can be masked with a screen so as to prevent light that is emitted directly from reaching the illumination field. Thus, there are no longer any interfering halos on the illumination field.

With this arrangement, a collimator is obtained that can form a small illumination spot and that has a smaller height, and thus a lower manufacturing cost.

The surgical lighting device comprises a lighting dome having a plurality of lighting devices as defined above.

With this arrangement, the lighting dome of the surgical lighting device is compact and makes it possible to generate, on the operative field, a small illumination spot having a diameter of in the range 4 centimeters (cm) to 30 cm when the lighting dome is at a distance from the operative field lying in the range 70 cm to 150 cm.

BRIEF DESCRIPTION OF THE DRAWING

The present invention can be better understood and other advantages appear on reading the following detailed description given merely by way of non-limiting example and with reference to the accompanying drawing, in which.

DESCRIPTION OF AN EMBODIMENT

Figure 1:
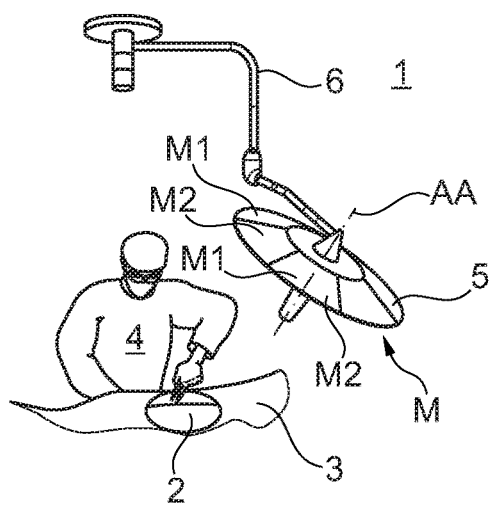
FIG. 1 is a diagrammatic perspective view of a surgical lighting device of the invention that is used in an operating theater.

FIG. 1 shows a surgical lighting device of the invention that is used in an operating theater to form an illumination spot 2 of small size on an operative field 3, e.g. on the body of a patient being operated on by a surgeon 4.

In this example, the lighting device 1 has a lighting dome 5 of the type suspended from the ceiling of the operating theater via an articulated suspension arm B.

As shown diagrammatically in FIG. 1, in this example the lighting dome 5 has a plurality of segments each forming a respective lighting module M.

Each lighting module, such as M1, M2, may be provided with a plurality of light sources associated with respective ones of a plurality of collimators that are directed so as to concentrate the light flux from the light sources onto the illumination spot 2 that is centered on the illumination axis AA of the lighting dome 5.

The illumination spot 2 is typically situated in the range 0.7 meters (m) from the lighting dome 5 to 1.5 m therefrom.

In general, the illumination spot 2 may have a diameter in the range a few centimeters to several tens of centimeters.

In this example, the light sources in the different modules M1, M2 are fed selectively and individually with electricity by one or more electrical power supply units (not shown) coupled to a monitoring and control unit (not shown). The various light sources can thus be fed with different and variable currents I.

Figure 2:
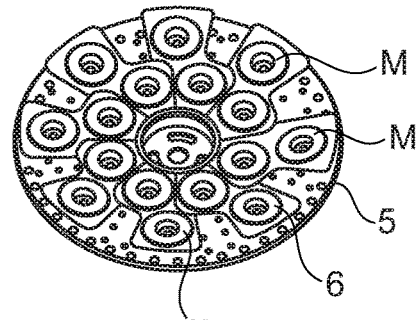
FIG. 2 is a diagrammatic perspective view of the underside of a lighting dome including collimators of the invention.

FIG. 2 shows an example of a lighting dome 5 seen from below, and on which it is possible to see collimator profiles 6, 6' coming from a plurality of lighting modules M.

Figure 3:
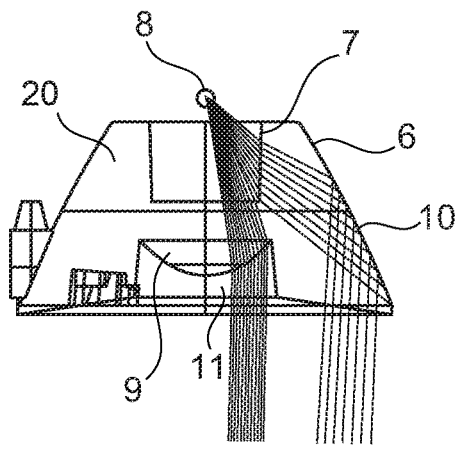
FIG. 3 is a diagram showing, in principle, the total internal reflection and the refraction of the light rays generated by a light source in a prior art solid collimator.

FIG. 3 shows a prior art standard solid collimator 6. The standard collimator is in the form of a truncated cap 20 having an inside surface 10 operating in total internal reflection. The truncated cap has a small base and a large base. In the small base, the cap has a frustoconical first recess 7 that is coaxial with the cap, the large base of the truncated cone 7 being open and coinciding with the small base of the cap. The small base of the frustoconical recess 7 is closed. The two inside surfaces of the truncated cone 7 and the small base of the truncated cone 7 refract the beams of incident light emitted by a light source 8 placed above the opening in the truncated cone 7, at the level of the tip of the cap.

A second recess 11 that is coaxial with the cap and in alignment with the first recess is arranged below the truncated cone 7. The second recess 11 has an optical interface such as a lens, so as to refract the received light beams towards the operative field 3.

The inside surface 10 reflects the received light beams towards the operative field 3.

In known manner, the standard collimator 6 combines the light refracted by the optical interface 9 with the light reflected by the inside surface 10 at a point on the operative field so as to form an illumination spot 2.

Figure 4:
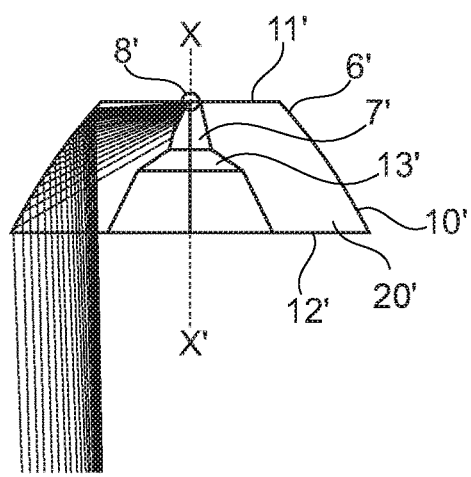
FIG. 4 is a diagram showing, in principle, the reflection and the refraction of the light rays generated by a light source in a solid collimator of the invention.

FIG. 4 shows a collimator 6' of the invention. The collimator 6' of the invention is, in this example, in the form of a truncated cap 20' having an inside surface 10' operating in total internal reflection. This cap 20' extends in an axial direction XX' between a small base 11' and a large base 12'.

A light source 8', e.g. an LED, is arranged centrally relative to the small base 11' of the truncated cap 20'. The collimator 6' guides the light beams towards the large base 12'.

The small base 11' opens into a through recess 7'. This recess has the shape of a truncated cone arranged axially to the cap with a small base open and coinciding with the small base 11' of the cap, and a large base facing towards the large base 12' of the cap 20'.

The optical interface formed by the walls of the recess 7' refract the light emitted by the light source 8' towards the inside surface 10' of the cap.

Figure 5:
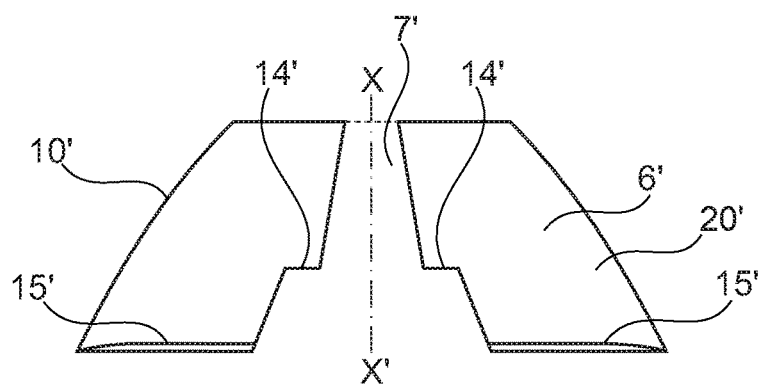
FIG. 5 is a diagrammatic profile view of a solid collimator of the invention.

In accordance with the invention, and as can be seen in FIGS. 4 and 5, the recess comprises a frustoconical first recess 7' having its small base open and coinciding with the small base 11' of the cap, and a second recess, which is in the form of a second truncated cone in this example, and which is arranged in alignment under the first recess. Since the recess comprising the first and second recesses is a through recess, it opens out in the large base 12' of the cap, and thus has a hole facing towards the operative field 3. Between the first and second recesses, an annular shoulder 14' is provided that forms a plane surface perpendicular to the axis of the cap or a flat, as can be seen in FIG. 5.

A screen may be arranged on this shoulder 14' so as to prevent the light beams from passing through the hole.

The screen 13' may be absorbent or diffusive on the side closer to the light source 8'. For example, the screen 13' may be in the form of a sticker or patch adhesively bonded to the flat so as to block off the hole. The screen 13' may also be in the form of a cover integrated by any known fastening means into the support of the collimator 6' in the lighting dome 5. The screen 13' may also be snap-riveted. The screen 13' may be clipped.

It should be noted that, in this example, only the frustoconical first recess 7' is functional optically.

It is also possible to have more than two recesses arranged in alignment on a common axis.

As shown in FIG. 5, due to the through recess, the large base 12' of the cap of the solid collimator 6' is an annular optical interface 15' that is refractive so as to focus the light beams towards the operative field 3 to form the illumination spot 2.

The large base 12' may be plane, but, in accordance with the invention, it may also be concave or convex. Under certain conditions, the large base 12' could also have a structure having micro-lenses.

The solid collimator 6' of the invention is rigid.

The solid collimator 6' is made of injection-molded plastics, as can be seen in part in FIG. 5. It may be made of PMMA.

The collimator 6' could also be machined directly from solid plastic.

As indicted above, with a standard collimator as shown in FIG. 3 and a given LED, in order to form an illumination spot, it is necessary to increase the height and the diameter of the standard collimator relative to a standard collimator that gives a large illumination spot.

By way of example, for a light source having a given LED, in order to form an illumination spot that is 215 millimeters (mm) in diameter with optical efficiency of 80%, a standard collimator must measure 26 mm in diameter and 14 mm in height. With the same LED, in order to form an illumination spot that is 63 mm in diameter with optical efficiency of 72%, the standard collimator must measure 92 mm in diameter and 52 mm in height. Therefore, in known manner, for a given LED, the smaller the illumination spot is to be, the larger the diameters and heights of the collimator need to be.

Still with the same LED, in order to form an illumination spot having a diameter of 79 mm, the standard collimator must have a diameter of 85 mm and a height of 48 mm, whereas in order to form the same illumination spot, a collimator of the invention has a diameter of 74 mm and a height of 26 mm. Thus, in order to obtain the same illumination spot, it is possible to make a saving of 46% in the height of the collimator by using a collimator of the invention. With a collimator of the invention, it is then possible to reduce the thickness of a lighting dome of a surgical lighting device. In addition, since the height of the collimator of the invention is smaller than the height of a standard collimator, the cost of the collimator of the invention as made of injection-molded plastic is therefore lower.

In a lighting device 1, each lighting module M may be provided with a plurality of light sources 8' associated with respective ones of a plurality of collimators 6' of the invention that are then directed to concentrate the light flux from the light sources 8' onto the illumination spot 2 that is centered on the illumination axis AA of the lighting dome 5.

In accordance with the invention, the small illumination spot that is formed has a diameter lying in the range 4 cm to 30 cm when the lighting dome 5 is at a distance from the operative field lying in the range 70 cm to 150 cm.

In a lighting dome 5, it is possible to have a mixture of standard collimators 6 for forming a large illumination spot and of collimators 6' of the invention for forming a small illumination spot.

In accordance with the invention, by the currents of the LEDs coupled to the standard collimators 6 being controlled separately from the currents of the LEDs coupled to the collimators 6' of the invention, it is possible to adjust the diameter of the illumination spot.

In a lighting dome 5, it is also possible to have a mixture of collimators 6' of the invention so as to form different small illumination spots, of diameter d1 and d2, where d1 is different from d2, optionally in combination with standard collimators 6 so as to form one large illumination spot.

In accordance with the invention, the light source 8' may be an LED, a Chip-On-Board (COB) LED, a laser diode coupled to a phosphor element, a color multi-chip LED, or indeed a matrix of LEDs.

In accordance with the invention, the light source 8' may be arranged very close to the collimator 6'. The rays close to the axis are lost, giving rise to a loss of light energy. However, this loss of light energy is not very significant because in order to form a small illumination spot, less light energy is required.

Naturally, the present invention is in no way limited to the above description of certain embodiments, which can undergo modifications without going beyond the ambit of the invention.

What is claimed is:

1. A surgical lighting device forming an illumination spot, comprising:
    a lighting dome having a plurality of lighting devices,
    wherein each lighting device includes a solid optical collimator comprising a truncated cap having an inside surface operating in total internal reflection and having a small base opening into a frustoconical through recess that is coaxial with said cap and at the centre of which a light source is placed, and having a refractive large base such that incident light emitted by said light source is guided in totality by said inside surface towards said large base of said cap, and
    wherein said recess of said collimator is disposed in said cap in such a manner as to have a small base open and coinciding with said small base of said cap, and in that said collimators are directed to concentrate the light flux from said light sources onto said illumination spot that is centered on the illumination axis of said lighting dome.

2. The surgical lighting device according to claim 1, wherein said recess in said collimator opens out into said large base of said cap.

3. The surgical lighting device according to claim 2, wherein said recess comprises a frustoconical first recess having a small base open and coinciding with said small base of said cap, and a second coaxial recess under said first recess and, between the two recesses, an annular shoulder carries a screen for said incident light.

4. The surgical lighting device according to claim 3, wherein said screen is absorbent on its side closer to the light source.

5. The surgical lighting device according to claim 3, wherein said screen is diffusive on its side closer to the light source.

6. The surgical lighting device according to claim 5, wherein said screen is adhesively bonded to said shoulder.

7. The surgical lighting device according to claim 3, wherein said shoulder forms a plane surface that is perpendicular to the axis of said cap.

8. The surgical lighting device according to claim 7, wherein said collimator is rigid.

9. The surgical lighting device according to claim 8, wherein said collimator is made of injection-molded plastic.

10. The surgical lighting device according to claim 9, wherein said collimator is made of PMMA.

11. The surgical lighting device according to claim 3, wherein a support of the collimator includes means for fastening said screen for said incident light.

12. The surgical lighting device according to claim 11, wherein said light source is an LED.

13. The surgical lighting device according to claim 3, wherein said screen is adhesively bonded to said shoulder.

14. The surgical lighting device according to claim 1, wherein said collimator is rigid.

15. The surgical lighting device according to claim 1, wherein said collimator is made of injection-molded plastic.

16. The surgical lighting device according to claim 1, wherein said collimator is made of PMMA.

17. The surgical lighting device according claim 1, wherein said light source is an LED.

* * * * *